(12) United States Patent
Lakner et al.

(10) Patent No.: US 8,378,239 B2
(45) Date of Patent: Feb. 19, 2013

(54) HERMETIC FEED-THROUGH WITH HYBRID SEAL STRUCTURE

(75) Inventors: Gabe Lakner, Mason, OH (US); Jian Sun, Mason, OH (US); Prasad S. Khadkikar, West Chester, OH (US)

(73) Assignee: Emerson Electric Co., St. Louis, MO (US)

( * ) Notice: Subject to any disclaimer, the term of this patent is extended or adjusted under 35 U.S.C. 154(b) by 269 days.

(21) Appl. No.: 12/808,452

(22) PCT Filed: Dec. 24, 2008

(86) PCT No.: PCT/US2008/088267
§ 371 (c)(1),
(2), (4) Date: Jun. 16, 2010

(87) PCT Pub. No.: WO2009/086435
PCT Pub. Date: Jul. 9, 2009

(65) Prior Publication Data
US 2011/0108320 A1     May 12, 2011

Related U.S. Application Data

(60) Provisional application No. 61/017,352, filed on Dec. 28, 2007.

(51) Int. Cl.
*H05K 3/10* (2006.01)
(52) U.S. Cl. ............ 174/650; 174/50.56; 174/667; 174/152 GM; 361/302
(58) Field of Classification Search ............ 174/152, 174/50.52, 50.59, 50.61, 650, 50.56, 667, 174/152 GM, 50.5, 50.55, 527, 262; 361/302; 439/587, 287
See application file for complete search history.

(56) References Cited

U.S. PATENT DOCUMENTS

| | | | | |
|---|---|---|---|---|
| 4,308,323 | A | * 12/1981 | Bowsky | 429/181 |
| 4,514,590 | A | * 4/1985 | Kyle | 174/152 GM |
| 4,833,049 | A | 5/1989 | Teaford et al. | |
| 4,913,673 | A | * 4/1990 | Kobler | 439/736 |
| 4,940,858 | A | 7/1990 | Taylor et al. | |
| 5,026,302 | A | 6/1991 | Spencer | |
| 5,535,512 | A | * 7/1996 | Armogan | 29/877 |
| 5,851,222 | A | * 12/1998 | Taylor et al. | 607/36 |
| 6,107,566 | A | 8/2000 | Quadir et al. | |
| 6,368,451 | B1 | 4/2002 | Goulette et al. | |
| 6,632,104 | B2 | 10/2003 | Quadir | |
| 6,696,199 | B2 | * 2/2004 | Yoshida et al. | 429/182 |
| 6,841,731 | B1 | * 1/2005 | Zanello | 174/50.56 |
| 7,145,076 | B2 | * 12/2006 | Knappen et al. | 174/50.6 |
| 7,210,966 | B2 | 5/2007 | Taylor et | |
| 7,396,265 | B2 | 7/2008 | Darley et al. | |
| 7,480,988 | B2 | 1/2009 | Ok et al. | |
| 2002/0139556 | A1 | 10/2002 | Ok et al. | |

(Continued)

FOREIGN PATENT DOCUMENTS
WO   WO 2007/087487 A1   8/2007

*Primary Examiner* — Angel R Estrada
*Assistant Examiner* — Dimary Lopez
(74) *Attorney, Agent, or Firm* — Harness, Dickey & Pierce, P.L.C.

(57) ABSTRACT

A power terminal feed-through includes a housing body, a plurality of conductive pins, and a seal structure that hermetically seals the conductive pins to the housing body and electrically insulates the conductive pins from the housing body. The seal structure includes a first material fused to one of the housing body and the conductive pin, and a second material fused to the other one of the housing body and the conductive pin. The first and second materials may be properly chosen to match thermal expansion of the housing body and the conductive pins, respectively.

17 Claims, 8 Drawing Sheets

U.S. PATENT DOCUMENTS

| | | |
|---|---|---|
| 2005/0092507 A1 | 5/2005 | Marshall et al. |
| 2006/0141861 A1 | 6/2006 | Darley et al. |
| 2007/0243762 A1 | 10/2007 | Burke et al. |
| 2008/0060844 A1 * | 3/2008 | Teske et al. .................. 174/667 |

* cited by examiner

HERMETIC FEED-THROUGH WITH HYBRID SEAL STRUCTURE

CROSS-REFERENCE TO RELATED APPLICATIONS

The present application claims the benefit of U.S. Provisional Application No. 61/017,352, filed on Dec. 28, 2007, and titled "Hermetic Terminal Having Multiple Sealing Materials." The entire disclosure of the above application is incorporated herein by reference.

FIELD

The present disclosure relates to electric power terminals, and more particularly to hermetic feed-throughs of the electric power terminals with improved seal structures.

BACKGROUND

This section provides background information related to the present disclosure which is not necessarily prior art.

Hermetically sealed electric power terminals generally include air-tight feed-throughs for use in conjunction with hermetically sealed devices. The feed-through includes a metal housing to be mounted on the hermetically sealed device, and a plurality of conductive pins extending through the metal housing for conducting electric current. A sealing material is generally provided between the metal housing and the conductive pins to electrically insulate the conductive pins from the metal housing. In addition, the sealing material hermetically seals the conductive pins to the metal housing to prohibit air leakage into or from the hermetically sealed device.

A glass or polymer has been used as the sealing material in the feed-through to provide electric insulation and prevent gas permeation. The performance, cost or design flexibility of a glass or polymer, however, may not be preferred for all purposes or environments or operating conditions. For example, some sealing materials may be used with a limited number of metals. Therefore the selection of metals for the conductive pins and housings is likewise limited.

SUMMARY

This section provides a general summary of the disclosure, and is not a comprehensive disclosure of its full scope or all of its features.

In one form, a hermetic feed-through includes a housing body, a conductive pin, and a seal structure that seals the conductive pin to the housing body and that provides electric insulation between the housing body and the conductive pin. The seal structure includes a first material fused (e.g., bonded or sealed) to one of the housing body and the conductive pin, and a second material fused to the other one of the housing body and the conductive pin.

In another form, a hermetic feed-through includes a housing body, a conductive pin, and a seal structure that seals the conductive pin to the housing body and that provides electric insulation between the housing body and the conductive pin. The seal structure includes a first material, a second material, and at least two of a first sealing path, a second sealing path, and a third sealing path. The first sealing path is a glass-to-metal seal. The second sealing path is a polymer-to-metal seal. The third sealing path is a polymer-to-glass seal.

In still another form, a method of manufacturing a feed-through includes: fusing a first material to at least one dummy pin to form a substrate; removing the at least one dummy pin from the substrate to form at least one opening corresponding to the dummy pin; inserting at least one conductive pin to the at least one opening; and fusing a second material to the at least one conductive pin.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 8A to 8D are cross-sectional views of the feed-through of FIG. 5, illustrating sequential steps of manufacturing the feed-through;

Corresponding reference numerals indicate corresponding parts throughout the several views of the drawings.

DETAILED DESCRIPTION

Example embodiments will now be described more fully with reference to the accompanying drawings.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

First Embodiment

Figure 1:
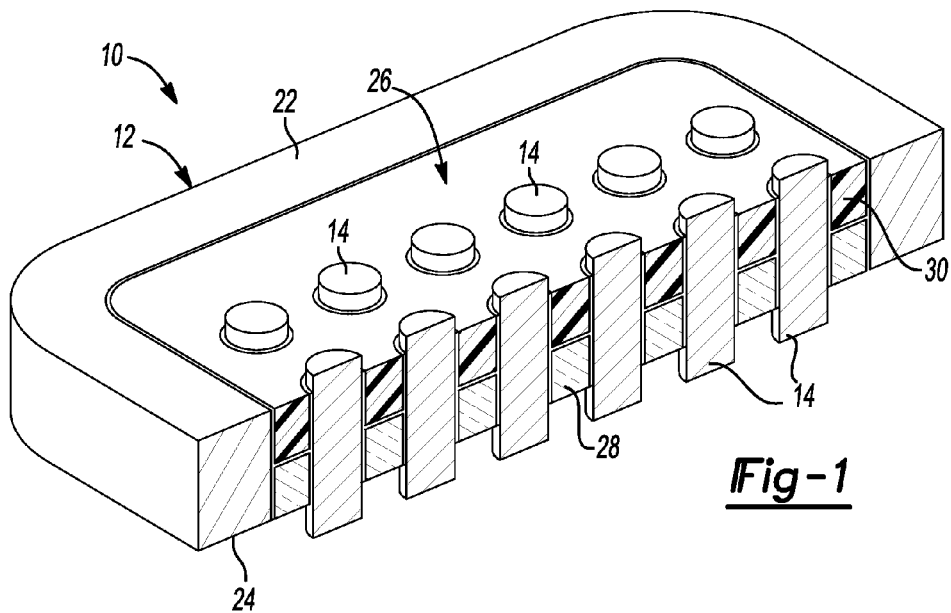
FIG. 1 is a partial cross-sectional perspective view of an exemplary feed-through of a first embodiment of the present disclosure.
Figure 4A:
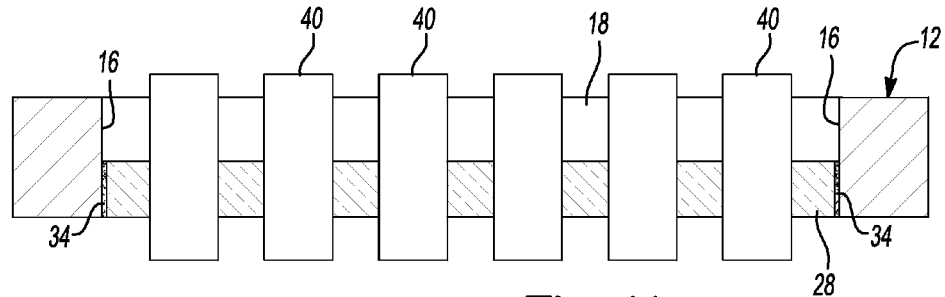
FIGS. 4A to FIG. 4D are cross-sectional views of the feed-through of FIG. 1, illustrating sequential steps of manufacturing the feed-through of the first embodiment.
Figure 4B:
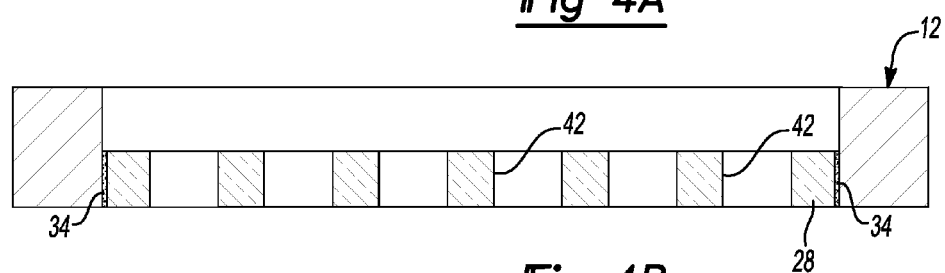
Figure 4C:
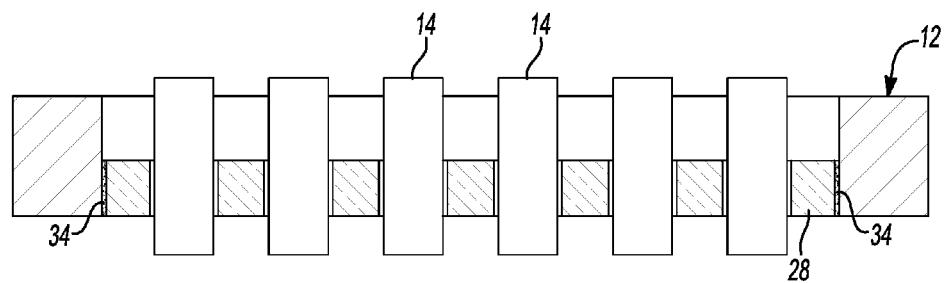
Figure 4D:
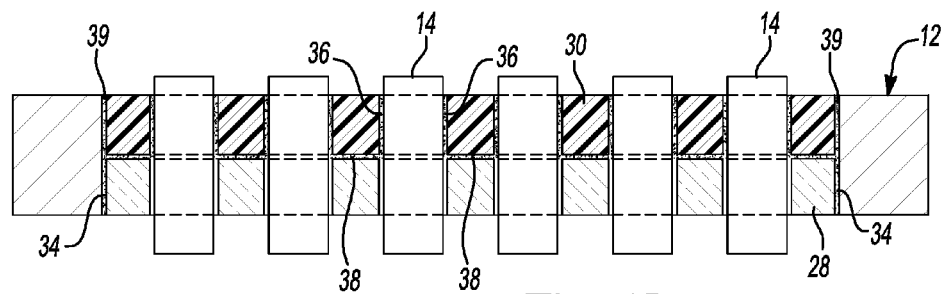

Referring to FIG. 1, an electric power terminal feed-through 10 in accordance with a first embodiment of the present disclosure includes a metallic housing body 12 and a plurality of conductive pins 14. The housing body 12 includes an inner surface 16 defining an inner space 18 (shown in FIG. 4A). The plurality of conductive pins 14 extend through the inner space 18 along a central axis Y of the housing body 12.

The feed-through 10 has a first side 22 and a second side 24 opposite to the first side 22. The feed-through 10 is mounted to a hermetically sealed device (not shown), for example, a disc drive, wherein the first side 22 is located inside the hermetically sealed device and the second side 24 is located outside the hermetically sealed device. A seal structure 26 is provided in the inner space 18 to seal the conductive pins 14 to the inner surface 16 of the housing body 12. The seal structure 26 electrically insulates the conductive pins 14 from the housing body 12 and hermetically blocks air flow from the first side 22 to the second side 24 of the feed-through 10. The seal structure 26 precludes leakage into or from the hermetically sealed device (by way of the conductive pins 14).

The housing body 12 may be made of cold-rolled steel. The conductive pins 14 may include a metal having a low melting point, such as copper, gold, and silver. The conductive pins 14 may also be copper pins, stainless steel pins coated with gold, or copper-core steel wires.

The seal structure 26 has a laminated structure including a first material and a second material. The first material and the second material have different fusing temperatures, gas permeation prevention properties, and/or coefficients of thermal expansion. For example, the first material may be selected to function as a gas barrier to prevent gas, particularly helium, from travelling through the seal structure 26. The second material may be selected for its low fusing temperature so that the seal structure 26 may be fused to the conductive pins and/or housing body at a lower fusing temperature than that of the first material, without damaging the housing body and/or conductive pins. Moreover, the first material and the second material may be chosen to have thermal expansion characteristics that match the metals (i.e., conductive pins and housing body) to which they are fused.

For example, the first material may be a sealing glass that can effectively prevent gas permeation. The second material may be a sealing polymer that has a lower fusing temperature than glass and can be fused to metals that have low melting points, such as aluminum, gold, copper, and silver. Alternatively, the first and second materials may have a thermal expansion matching the housing body and the conductive pins, respectively, to avoid damaging the sealing paths at elevated temperatures. Alternatively, both the first material and the second material may be polymers that have different required properties as previously described.

Figure 2:
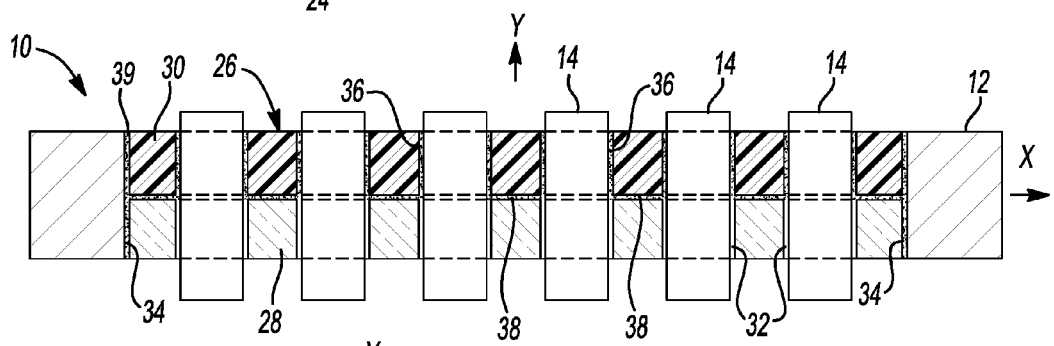
FIG. 2 is a cross-sectional view of the feed-through of FIG. 1.

Referring to FIG. 2, the seal structure 26 includes a glass layer 28 and a polymer layer 30 that are arranged along the central axis Y of the housing body 12. The seal structure 26 defines a plurality of openings. The conductive pins 14 are inserted into the openings.

Figure 3:
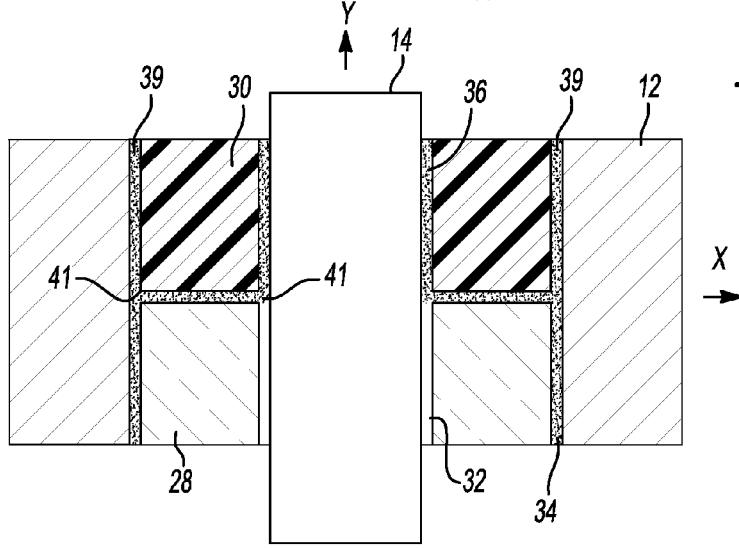
FIG. 3 is a schematic view illustrating sealing paths of the feed-through of FIG. 1.

Referring to FIG. 3, the seal structure 26 includes a first sealing path 34, a second sealing path 36, and a third sealing path 38 that are continuously connected to form a continuous sealing boundary. It should be noted that the interfaces of the sealing paths, themselves, may be smooth and featureless or include features such as serrations, locking fingers and the like to promote a good seal.

The first, second, and third sealing paths 34, 36, and 38 are provided at interfaces between the glass layer 28 and the inner surface 16 of the housing body 12, between the polymer layer 30 and the conductive pins 14, and between the glass layer 28 and the polymer layer 30, respectively. Angled portions 41 may be formed at their connecting points, particularly, at the interface between the two sealing materials. Optionally, a fourth sealing path 39 may be provided at an interface between the housing body 12 and the polymer layer 30. The first sealing path 34 and the second sealing path 36 provide a hermetic seal. The third sealing path 38 may or may not provide a hermetic seal.

The first sealing path 34 is a glass-to-metal seal that fuses the glass to the housing body 12 made of cold-rolled steel. The glass layer 28 may be selected to have a coefficient of thermal expansion that matches that of the housing body 12 to avoid compromising or interrupting the first sealing path 34 due to incompatible thermal expansion.

The second sealing path 36 is a polymer-to-metal seal, which seals the polymer to the gold-coated conductive pins 14. The polymer may be epoxy. The materials for the polymer layer 30 may be properly selected to have a coefficient of thermal expansion matching that of the conductive pins 14 to avoid compromising or interrupting the second sealing path 36 due to incompatible thermal expansion when the operating temperature changes.

The third sealing path 38 is a polymer-to-glass seal. The third sealing path 38, which is formed at the interface between the two sealing materials, may be oriented perpendicular to the conductive pins 14 and the inner surface 16 of the housing body 12. When the feed-through 10 is operated at elevated temperatures, shear stress may be generated at the third sealing path 38 due to a difference in thermal expansion between the two sealing materials. The shear stress does not compromise or interrupt the third sealing path 38. Therefore, the sealing paths among the first material, the second material, the housing body and the conductive pins remain continuously connected (i.e., closed) at elevated temperatures.

While not shown in the drawings, it is appreciated and understood that the third sealing path 38 does not have to be perpendicular to the conductive pins 14 and/or the housing body 12 to maintain a continuous sealing boundary when temperature changes. The third sealing path 38 may have an angle relative to the X axis so that the interface between the two sealing materials does not receive significant tensile stress to compromise or interrupt the third sealing path 38. The angle of the third sealing path 38 relative to the X axis may depend on coefficients of thermal expansion of the two sealing materials.

The fourth sealing path 39 is also a polymer-to-metal seal and can be optionally applied. The fourth sealing path is different from the second sealing path in that the second sealing path is provided between a polymer and a first metal that has a low melting point, whereas the fourth sealing path is provided between the polymer and a second metal that has a higher melting point.

Referring to FIGS. 4A to 4D, to form a feed-through 10 of the first embodiment, a plurality of dummy pins 40 are first provided in the inner space 18 of the housing body 12, followed by fusing a glass material to the dummy pins 40 and the inner surface 16 of the housing body 12 to form the glass layer 28. The first sealing path 34 is formed at the interface between the glass layer 28 and the housing body 12.

Next, the dummy pins 40 are removed to form a plurality of openings 42 in the glass layer 28. A plurality of conductive pins 14 are inserted into the openings 42, followed by fusing a polymer material to the conductive pins 14 and the glass layer 28 to form a polymer layer 30 on an upper surface of the glass layer 28. A second sealing path 36 and the third sealing path 38 are formed between the polymer layer 30 and the conductive pins 14 and between the glass layer 28 and the polymer layer 30, respectively. Optionally, the polymer material may be fused to the inner surface 16 of the housing body 12 to form the fourth sealing path 39.

Second Embodiment

Figure 5:
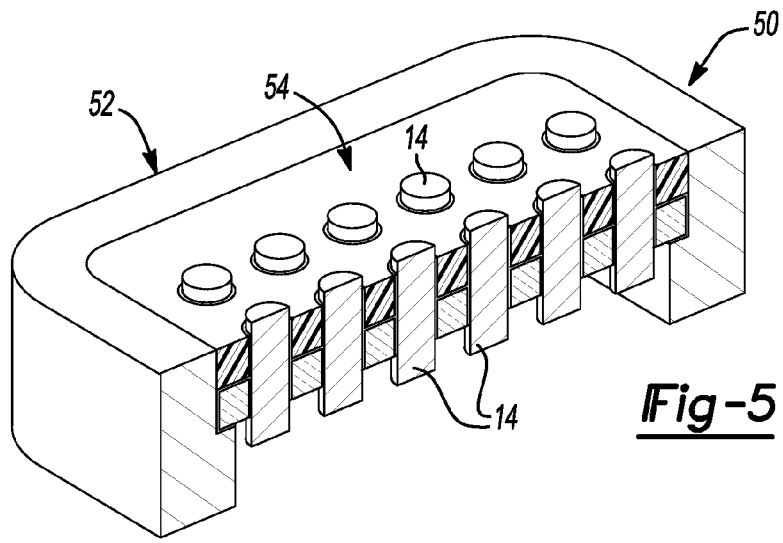
FIG. 5 is a partial cross-sectional perspective view of an exemplary feed-through of a second embodiment of the present disclosure.
Figure 6:
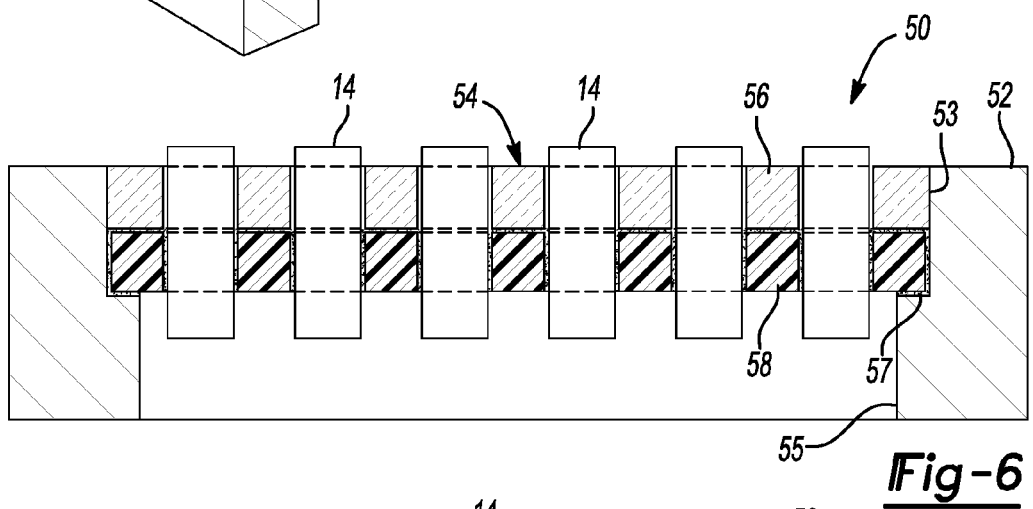
FIG. 6 is a cross-sectional view of an exemplary feed-through of a second embodiment of the present disclosure.

Referring to FIGS. 5 and 6, a power terminal feed-through in accordance with a second embodiment of the present disclosure has a structure similar to that of first embodiment except for the seal structure and the housing body.

The feed-through 50 includes a metallic housing body 52, a plurality of conductive pins 14, and a seal structure 54. The housing body 52 is made of aluminum, which has a low melting point. The housing body 52 may include an inner surface 53 and an annular flange 55 extending from the inner surface 53. The flange 55 includes a horizontal surface 57 perpendicular to the inner surface 53. The seal structure 54 includes a glass layer 56 and a polymer layer 58 formed between the glass layer 56 and the annular flange 55.

Figure 7:
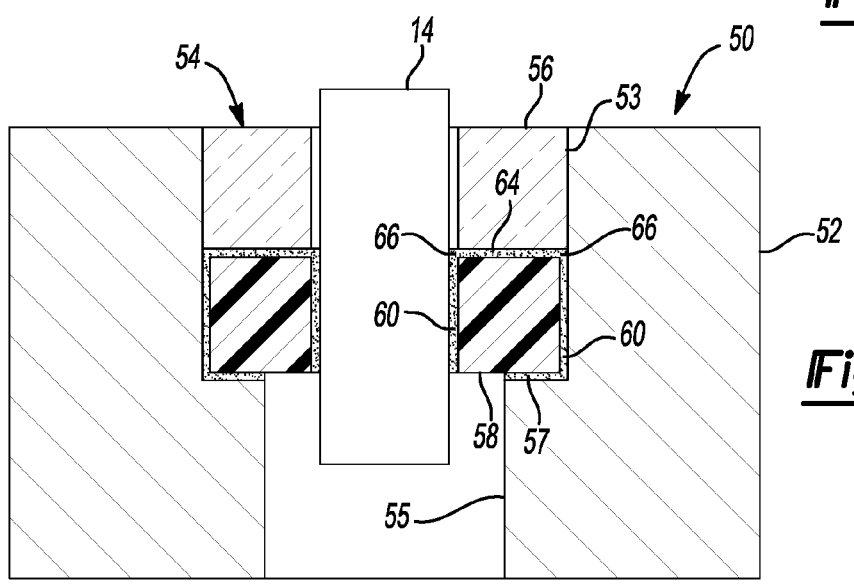
FIG. 7 is a schematic view illustrating sealing paths of the feed-through of FIG. 5.
Figure 8A:
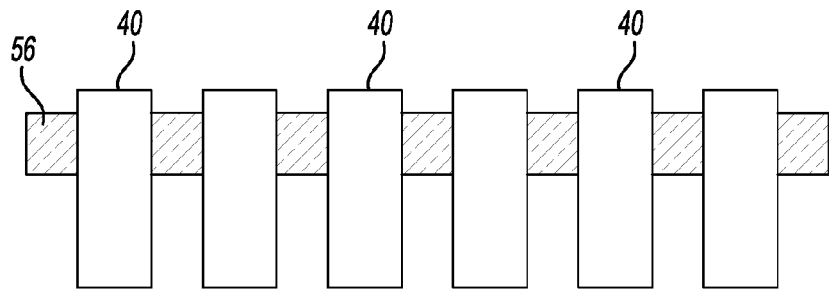
Figure 8B:
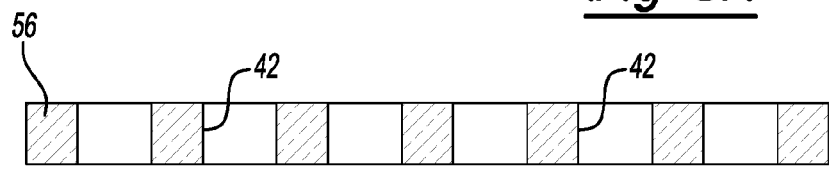
Figure 8C:
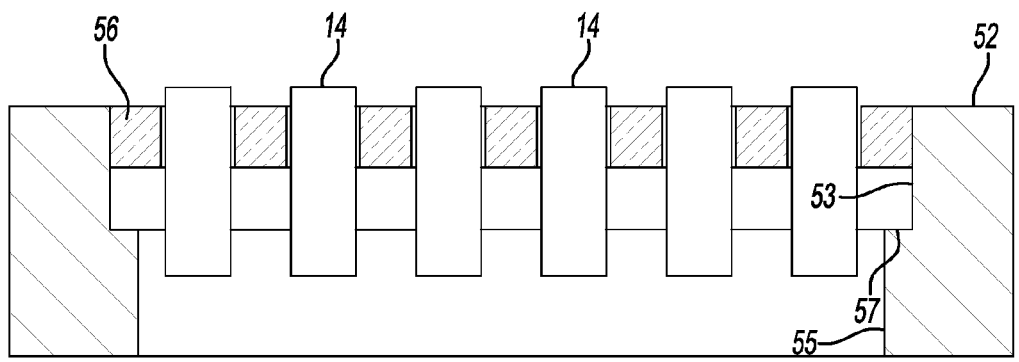
Figure 8D:
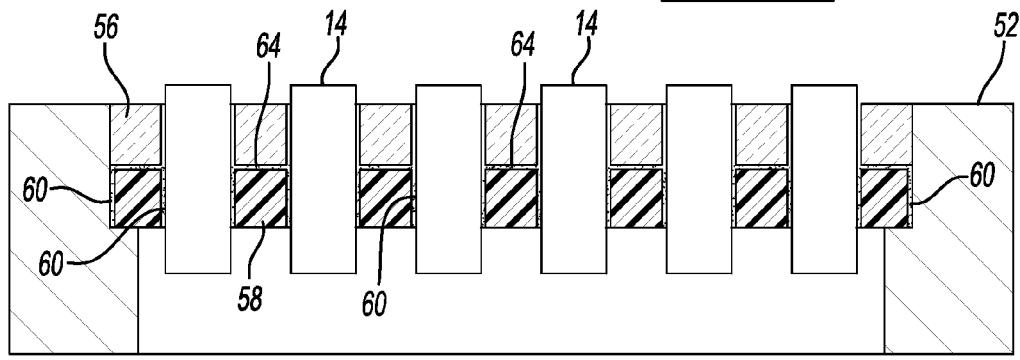

Referring to FIG. 7, the seal structure 54 includes a pair of second sealing paths 60, and a third sealing path 64 between the glass layer 56 and the polymer layer 58. The second sealing paths 60 are formed between the polymer layer 58 and the housing body 52 and between the polymer layer 58 and the conductive pins 14. The second sealing paths 60 are polymer-to-metal seals. A part of the second sealing paths 60 is formed between the polymer layer 58 and the horizontal surface 57 of the flange 55.

The third sealing path 64 is formed at an interface between the glass layer 56 and the polymer layer 58 and may be oriented perpendicular to the conductive pins 14 and the inner surface 53 of the housing body 52. The third sealing path 64 is a polymer-to-glass seal. The pair of second sealing paths 60 are connected by the third sealing path 64. Angled portions 66 are formed at their connecting points.

Referring to FIGS. 8A to 8D, to form the feed-through 50 of the second embodiment, a glass material (i.e., a glass pellet) is fused to a plurality of dummy pins 40 to form a glass layer 56 or a glass substrate. The dummy pins 40 are removed from the glass layer 56 to form a plurality of openings 42. A plurality of conductive pins 14 are inserted into the plurality of openings 42. The sub-assembly of the glass layer 56 and the conductive pins 14 is placed in the housing body 52. A polymer pellet (such as epoxy) is disposed in the space between the glass layer 56 and the upper horizontal surface 57 of the flange 55 to fuse the conductive pins 14 and the housing body 52. The second sealing paths 60 and the third sealing path 64 are formed when the polymer material is cured.

Third Embodiment

Figure 9:
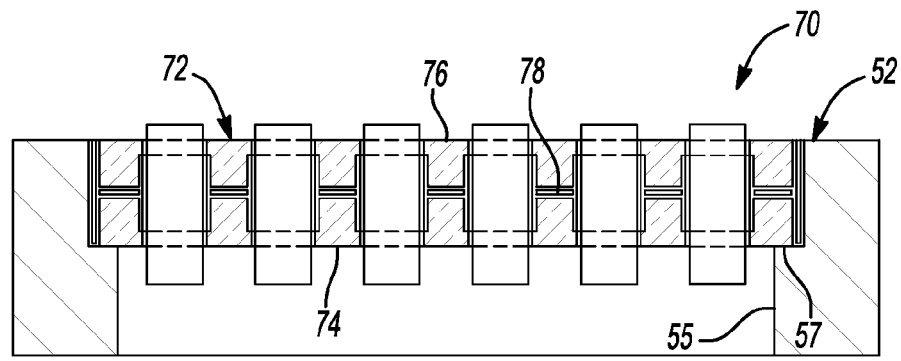
FIG. 9 is a cross-sectional view of an exemplary feed-through in accordance with a third embodiment of the present disclosure.

Referring to FIG. 9, a feed-through 70 in accordance with a third embodiment of the present disclosure includes a structure similar to that in the second embodiment except for a seal structure 72. The seal structure 72 includes a first glass layer 74, a second glass layer 76, and a polymer layer 78 between the first and second glass layers 74 and 76. The seal structure 72 has improved gas permeation prevention properties due to the presence of two glass layers 74 and 76 and can be fused to the conductive pins 14 and the housing body 52 having low melting points. The glass layers 74 and 76 may be properly chosen to have a thermal expansion matching that of the housing body 52. The polymer layer 78 may be properly chosen to have a thermal expansion matching that of the conductive pins 14.

Figure 10:
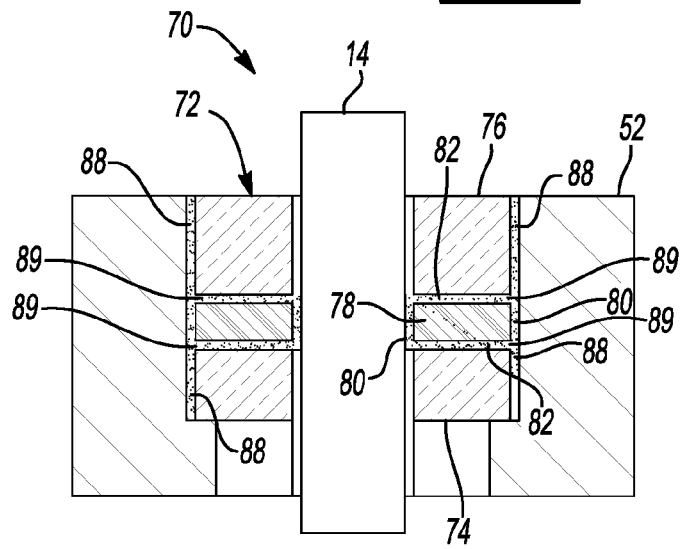
FIG. 10 is a schematic view illustrating sealing paths of a feed-through of a third embodiment.

Referring to FIG. 10, the seal structure 72 includes a pair of second sealing paths 80 and a pair of third sealing paths 82. The pair of second sealing paths 80 are formed at interfaces between the polymer layer 78 and the aluminum housing body 52 and between the polymer layer 78 and the conductive pins 14. The third sealing paths 82 are formed at interfaces between the polymer layer 78 and the first glass layer 74 and between the polymer layer 78 and the second glass layer 76. The second sealing paths 80 are polymer-to-metal seals. The third sealing paths 82 are polymer-to-glass seals.

Optionally, the seal structure 72 may include a plurality of fourth sealing paths 88 that are polymer-glass-metal seals, formed between the glass layers 74, 76 and the housing body 52. The second sealing paths 80, the third sealing paths 82, and the fourth sealing paths 88 are continuously connected to form a continuous sealing boundary that has angled portions 89.

To manufacture the feed-through 70 or 71 of the present embodiment, the first glass material and the second glass material are fused to dummy pins to form a first glass layer 74 and a second glass layer 76, respectively. After the first glass layer 74 and the second glass layer 76 are cured, the dummy pins are removed to form a plurality of openings that correspond to the conductive pins. The first glass layer 74 is placed in the inner space of the housing body 52 against the flange 55. A molten polymer material is then applied on the entire upper surface of the first glass layer 74.

Next, the second glass layer 76 is placed on the molten polymer material. The conductive pins 14 are then inserted into the openings. Next, the second glass layer 76 is pressed against the first glass layer 74. After the polymer layer 78 is cured, the seal structure that has a laminated structure is formed, as shown in FIG. 10.

Figure 11:
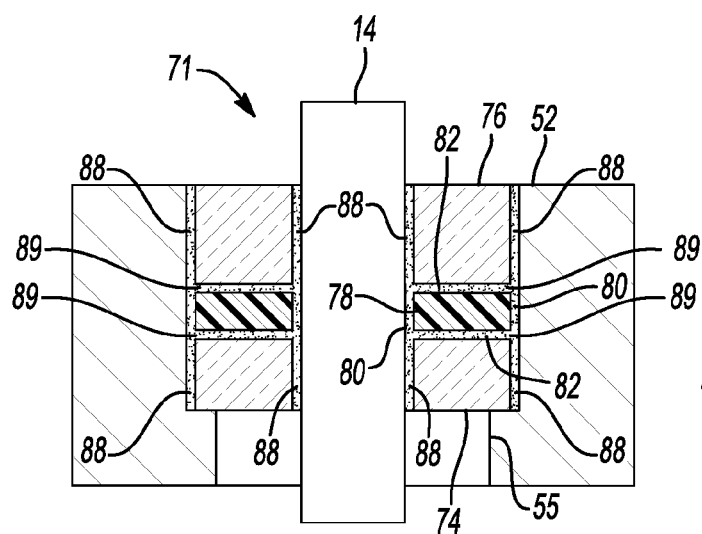
FIG. 11 is a schematic view illustrating sealing paths of a variant of an exemplary feed-through of a third embodiment.

Alternatively, gaps may be formed between the conductive pins 14 and the first glass layer 74 and the second glass layer 76, and between the housing body 52 and the first glass layer 74 and the second glass layer 76. Polymer pellets may be provided in the gaps to form additional sealing paths 88, as shown in FIG. 11.

Fourth Embodiment

Figure 12:
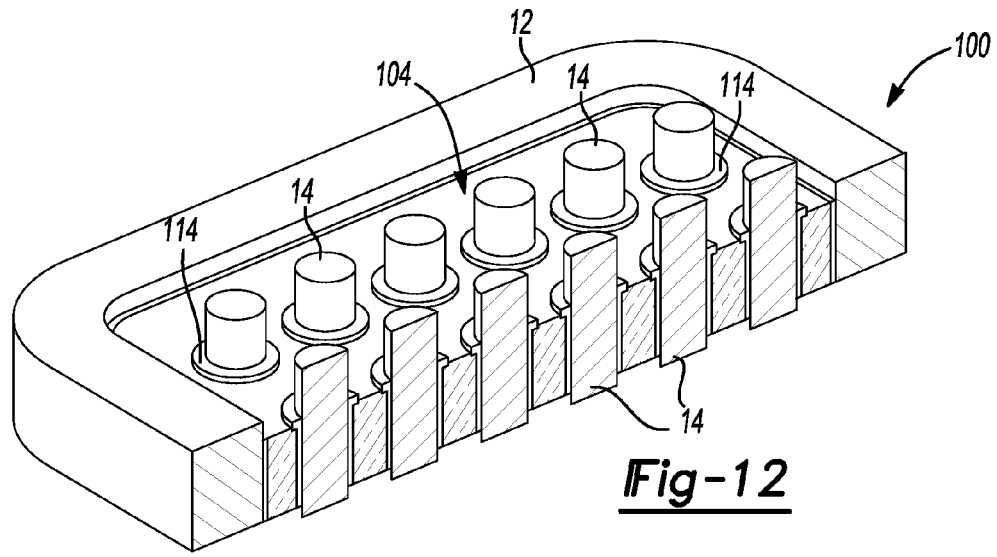
FIG. 12 is a partial cross-sectional perspective view of an exemplary feed-through in accordance with a fourth embodiment of the present disclosure.
Figure 13:
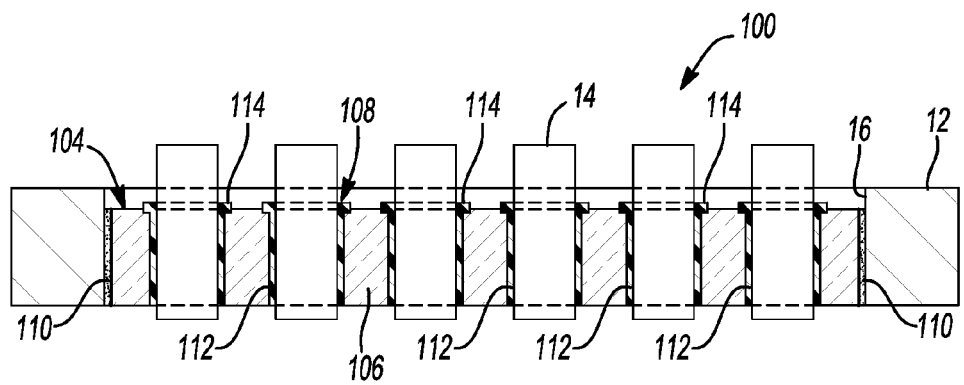
FIG. 13 is a cross-sectional view of a feed-through of the fourth embodiment.

Referring to FIGS. 12 and 13, a feed-through 100 in accordance with a fourth embodiment of the present disclosure has a housing body 12 made of cold-rolled steel, similar to that of the first embodiment. A seal structure 104 seals a plurality of conductive pins 14 to the housing body 12. The seal structure 104 includes a glass layer 106 and a plurality of polymer layers 108. The polymer layers 108 each have a tubular body 112 and a flange portion 114 extending perpendicularly and outwardly from the tubular body 112.

Figure 14:
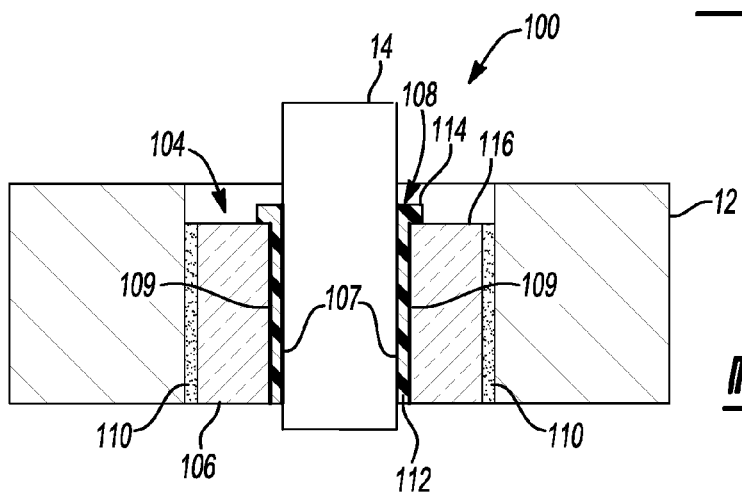
FIG. 14 is a schematic view illustrating sealing paths of an exemplary feed-through of the fourth embodiment.

Referring to FIG. 14, the glass layer 106 is fused to the inner surface 16 of the housing body 12 to form a first sealing path 110, i.e., glass-to-metal seal. The tubular bodies 112 of the polymer layers 108 are fused to the conductive pins 14 and the glass layer 106 to form second sealing paths 107 (i.e., polymer-to-metal seals) and third sealing paths 109 (i.e., polymer-to-glass seals). The flange portions 114 of the polymer layers 108 are fused to an upper surface 116 of the glass layer 106 to form polymer-to-glass seals.

To manufacture the feed-through 100 of the present embodiment, a glass material is fused to the housing body 12 and a plurality of dummy pins to form the glass layer 106. After the glass material is cured, the dummy pins are removed to create a plurality of openings in the glass layer 106. A plurality of conductive pins 14 are inserted into the openings. Polymer pellets are applied around the conductive pins 14 to form the tubular portions 112 between the glass layer 106 and the conductive pins 14. A portion of the polymer pellets may be formed on the upper surface 116 of the glass layer 106 to form the flange portions 114.

Fifth Embodiment

Figure 15:
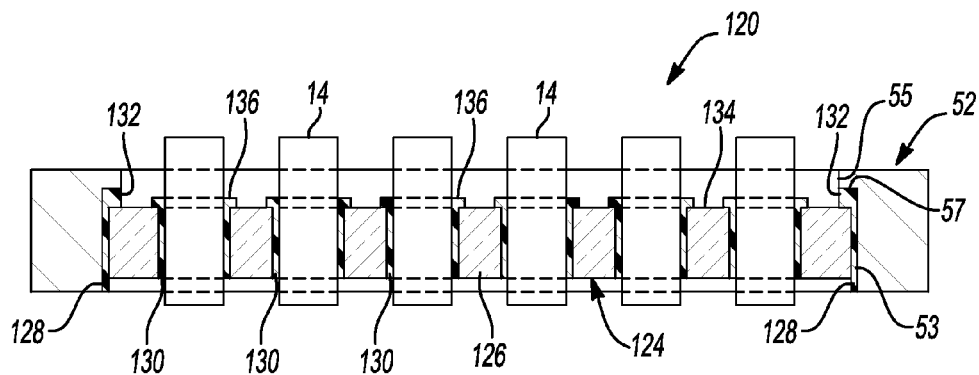
FIG. 15 is a cross-sectional view of an exemplary feed-through of the fifth embodiment of the present disclosure.
Figure 16:
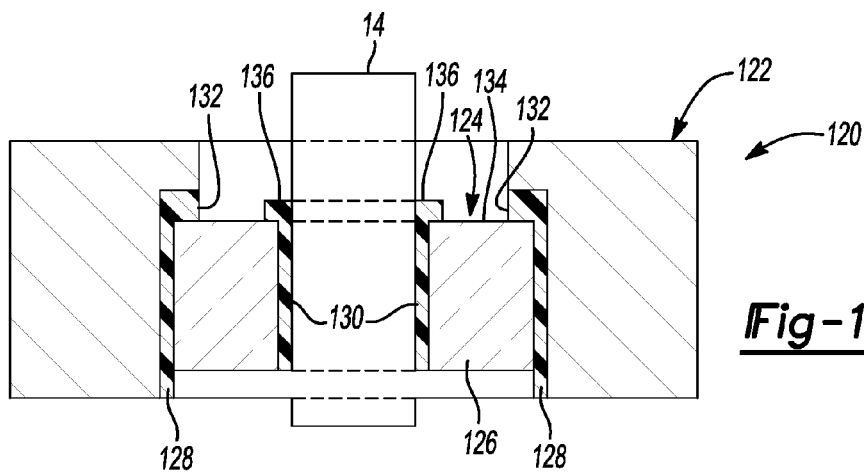
FIG. 16 is a schematic view illustrating sealing paths of a feed-through of the fifth embodiment.

Referring to FIGS. 15 and 16, a feed-through 120 in accordance with a fifth embodiment of the present disclosure is similar to the feed-through in the fourth embodiment except for the housing body and the seal structure. The housing body 52 of the present embodiment is similar to that of the second embodiment, which is made of aluminum. The seal structure 124 of the present embodiment is similar to the seal structure 104 of the fourth embodiment except that the glass layer 126 of the present embodiment is not fused to the housing body 52.

The glass layer 156 is fused to the inner surface of the housing body 12 to form a first sealing path 166, i.e., a glass-to-metal seal. The first polymer layer 158 and the second polymer layer 160 are fused to the conductive pins 14 to form a pair of second sealing paths 168, which are polymer-to-metal seals. Additionally, the first polymer layer 158 and the second polymer layer 160 are fused to the lower surface 162 and the upper surface 164 of the glass layer 156, respectively, to form a pair of third sealing paths 170, which are polymer-to-glass seals. The first sealing path 166, the pair of the second sealing paths 168, and the pair of the third sealing paths 170 are connected to form a continuous sealing boundary.

The seal structure 124 includes a pair of second sealing paths, which are polymer-to-metal seals and a pair of third sealing paths, which are glass-to-polymer seals.

Sixth Embodiment

Figure 17:
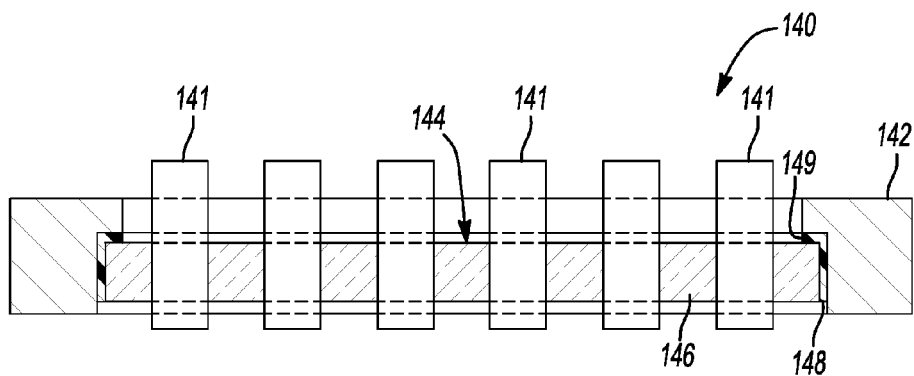
FIG. 17 is a cross-sectional view of a feed-through in accordance with a sixth embodiment of the present disclosure.
Figure 18:
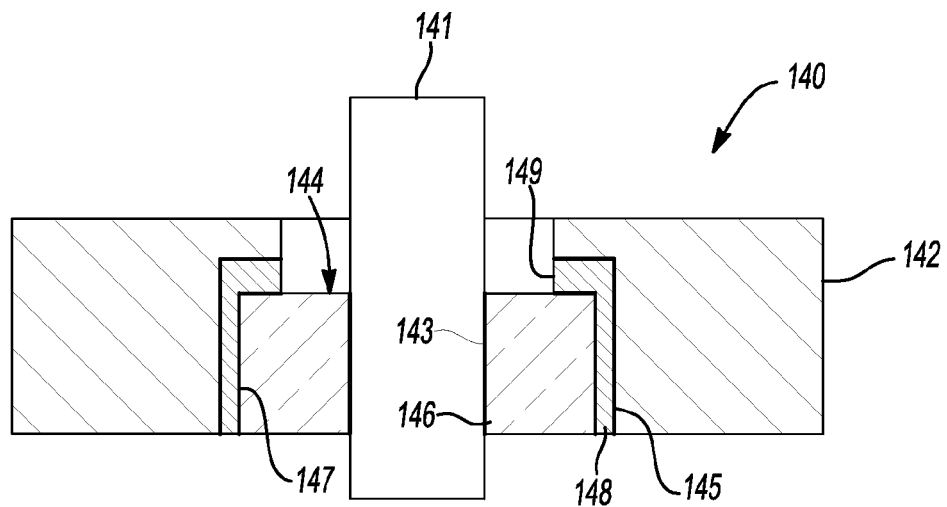
FIG. 18 is a schematic view illustrating a sealing boundary of a feed-through of the sixth embodiment.

Referring to FIGS. 17 and 18, a feed-through 140 in accordance with a sixth embodiment of the present disclosure is similar to the fifth embodiment, except for the seal structure and the conductive pins. The seal structure 144 has a glass layer 146 and a polymer layer having a second tubular body 148 and a flange portion 149 extending perpendicularly and inwardly from the second tubular body 148. The conductive pins 141 are palladium plated. Because the conductive pins 141 have a high melting point, the glass layer 146 can be directly fused to the conductive pins 141, thereby eliminating the first tubular bodies of the fourth embodiment.

The seal structure 144 has a first sealing path 143, a second sealing path 145, and a third sealing path 147. The first sealing path 143 is a glass-to-metal seal at an interface between the conductive pin 141 and the glass layer 146. The second sealing path 145 is a polymer-to-metal seal at an interface between the housing body 52 and the polymer material. The third sealing path 147 is a polymer-to-glass layer at an interface between the glass layer 146 and the polymer material.

Seventh Embodiment

Figure 19:
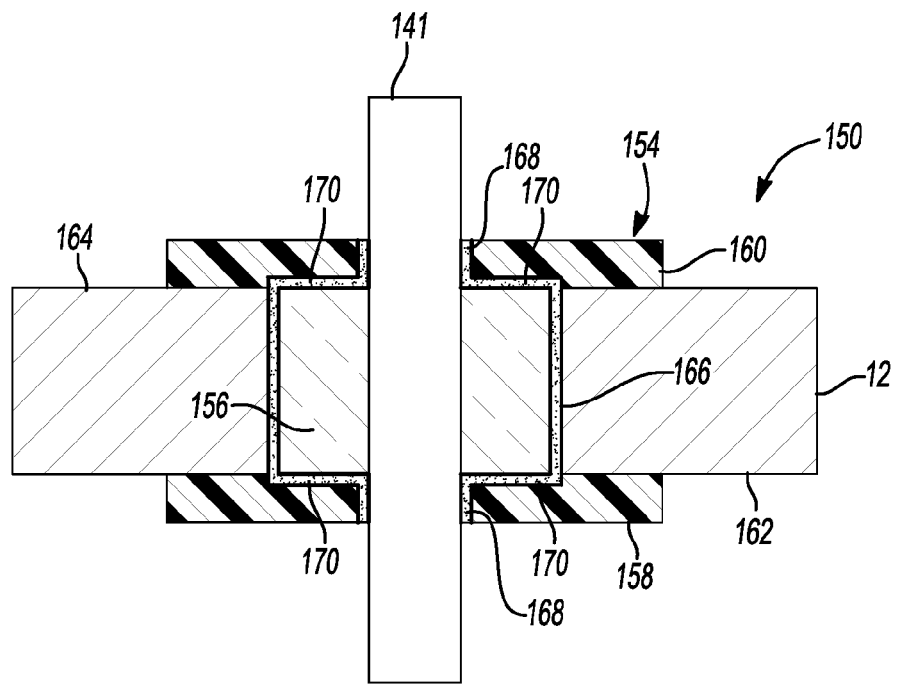
FIG. 19 is a schematic view illustrating a sealing boundary of a feed-through in accordance with a seventh embodiment of the present disclosure.

Referring to FIG. 19, a feed-through 150 in accordance with a seventh embodiment of the present disclosure includes a housing body 12, a conductive pin 14, and a seal structure 154. The housing body 12 and the conductive pins 14 are similar to those in the first embodiment. The housing body 12 is made of cold-rolled steel. The conductive pins 14 are gold-coated. The seal structure 154 includes a glass layer 156, a first polymer layer 158, and a second polymer layer 160. The glass layer 156 fills in the entire inner space of the housing body 12. The first polymer layer 158 and the second polymer layer 160 are formed on a lower surface 162 and an upper surface 164 of the housing body 12, respectively.

The glass layer 156 is fused to the inner surface of the housing body 152 to form a first sealing path 166, i.e., a glass-to-metal seal. The first polymer layer 158 and the second polymer layer 160 are fused to the conductive pins 14 to form a pair of second sealing paths 168, which are polymer-to-metal seals. Additionally, the first polymer layer 158 and the second polymer layer 160 are fused to the lower surface 162 and the upper surface 164 of the glass layer 156, respectively, to form a pair of third sealing paths 170, which are polymer-to-glass seals. The first sealing path 166, the pair of the second sealing paths 168, and the pair of the third sealing paths 170 are connected to form a continuous sealing boundary.

The hybrid seal structure that includes a first material and a second material according to any of the embodiments described in the present disclosure allows for a wide selection of materials for the seal structure, the housing body, and the conductive pins. The first material may be used to prevent gas permeation, whereas the second material may be used for fusing the seal structure to the conductive pins and/or housing body if the conductive pins and housing body have low melting points. Therefore, the hybrid seal structure can effectively prevent gas permeation without damaging the housing body and the conductive pins.

The polymers used in any of the embodiments described above may be a thermoset polymer or a thermoplastic polymer. A suitable thermoset polymer includes Rohm and Haas's Corvel™ ECB-1363A Red 2036. Testing of this material confirms that satisfactory hermetic seal(s) (with a gas permeation rate as low as $10^{-8}$ cm$^3$ He/sec at 1 atmosphere) in the hybrid seal structure are achieved. In addition, it is contemplated that suitable thermoplastic polymers for the disclosed construction may include Nanocor's Imperm™ 103 (a Nylon/Nanocomposite), Nylon 6,6, Ticona's Liquid Crystalline Polymer (glass-filled or no-glass-filled), Chevron Phillips's Polyphenylene Sulfide, Chevron Phillips's Polyphenylene Sulfide-Glass, Chevron Phillips's Polyphenylene Sulfide-glass and mineral, Dow's Saranex™ 11 co-polymer, EVAL™ Ethylene Vinyle Alcohol co-polymer, INEOS Barex's Polyacrylonitrile, and DuPont's Polybutylene terephthalate.

Further, the first and second materials may be properly selected to match the thermal expansion of the housing body and the conductive pins, respectively. Therefore, the hybrid seal structure can maintain integrity of the sealing paths at high temperatures.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention

What is claimed is:

1. A hermetic feed-through comprising:
a housing body;
a conductive pin; and
a seal structure that hermetically seals the conductive pin to the housing body and that provides electric insulation between the housing body and the conductive pin;
wherein the seal structure comprises a first material fused to one of the housing body and the conductive pin, and a second material fused to the first material and to the other one of the housing body and the conductive pin such that the seal structure comprises a first sealing path, a second sealing path, and a third sealing path that are connected to form a continuous sealing boundary.

2. The hermetic feed-through of claim 1, wherein the housing body is made of a first metal, the first metal having a coefficient of thermal expansion matching that of the first material, the conductive pin being made of a second metal, the second metal having a coefficient of thermal expansion matching that of the second material.

3. The hermetic feed-through of claim 2, wherein the first material has a gas permeation prevention property better than that of the second material.

4. The hermetic feed-through of claim 3, wherein the second material has a fusing temperature lower than that of the first material.

5. The hermetic feed-through of claim 1, further wherein the first sealing path is a glass-to-metal seal, the second sealing path is a polymer-to-metal seal, and the third sealing path is a glass-to-polymer seal; and
wherein the housing body is made of a first metal, the first metal having a coefficient of thermal expansion matching that of the first material, and the conductive pin is made of a second metal, the second metal having a coefficient of thermal expansion matching that of the second material.

6. The hermetic feed-through of claim 1, wherein the first material is glass, the second material is epoxy, the housing body is made of steel, and the conductive pin includes at least one of copper, silver, and gold.

7. The hermetic feed-through of claim 1, wherein the third sealing path forms an angled portion between the first material and the second material.

8. The hermetic feed-through of claim 1, wherein the seal structure further comprises a third material fused to the second material such that the seal structure comprises a fourth sealing path.

9. The hermetic feed-through of claim 8 wherein the first sealing path is a glass-to-metal seal, the second sealing path is a polymer-to-metal seal, the third sealing path is a glass-to-polymer seal, and the fourth sealing path is a glass-to-polymer seal.

10. The hermetic feed-through of claim 9, wherein the first and second sealing paths are parallel to one another; and
wherein the third and fourth sealing paths are parallel to one another.

11. A hermetic feed-through comprising:
a housing comprising an aperture therethrough;
a conductive pin having a longitudinal axis and extending in a direction along the longitudinal axis through the aperture in the housing; and
a seal structure hermetically sealing the conductive pin to the housing and electrically insulating the conductive pin from the housing;
the seal structure comprising a first dielectric material, a second dielectric material and at least three sealing paths extending parallel to the direction of the longitudinal axis, a first sealing path located between the first dielectric material and the housing, a second sealing path located between the second dielectric material and the pin, and a third sealing path located between the first dielectric material and the second dielectric material; and
wherein the first sealing path comprises a glass-to-metal seal, the second sealing path comprises a polymer-to-metal seal, and the third sealing path comprises a glass-to-polymer seal.

12. The hermetic feed-through of claim 11, wherein the second dielectric material comprises a flange portion extending perpendicularly to the longitudinal axis; and
wherein the seal structure further comprises a fourth sealing path extending perpendicularly to the direction of the longitudinal axis, the fourth sealing path located between the flange portion of the second dielectric material and first the dielectric material.

13. The hermetic feed-through of claim 11 wherein the first dielectric material comprises a sealing glass and the second dielectric material comprises a polymer; and
wherein the housing comprises a first metal having a coefficient of thermal expansion matching that of the sealing glass, and the conductive pin comprises a second metal having a coefficient of thermal expansion matching that of the polymer.

14. A hermetic feed-through comprising:
a housing comprising an aperture therethrough;
a conductive pin having a longitudinal axis and extending in a direction along the longitudinal axis through the aperture in the housing; and a seal structure hermetically sealing the conductive pin to the housing and electrically insulating the conductive pin from the housing;

the seal structure comprising a first dielectric material, a second dielectric material, a third dielectric material and four sealing paths extending parallel to the direction of the longitudinal axis, a first sealing path located between the first dielectric material and the housing, a second sealing path located between the second dielectric material and the pin, a third sealing path located between the first dielectric material and the third dielectric material, and a fourth sealing path located between the second dielectric material and the third dielectric material.

15. The hermetic feed-through of claim 14, wherein the housing comprises aluminum.

16. The hermetic feed-through of claim 14 wherein the first and second sealing paths comprise a polymer-to-metal seal, and the third and fourth sealing paths comprise a glass-to-polymer seal.

17. The hermetic feed-through of claim 14 wherein the first and third dielectric materials comprise a polymer, and the second dielectric material comprises a sealing glass; and wherein the housing comprises a first metal having a coefficient of thermal expansion matching that of the first dielectric material, and the conductive pin comprises a second metal having a coefficient of thermal expansion matching that of the third dielectric material.

* * * * *